(12) United States Patent
Haughton et al.

(10) Patent No.: US 10,292,760 B2
(45) Date of Patent: May 21, 2019

(54) COUPLER APPARATUS FOR COUPLING ELECTRICAL SIGNALS BETWEEN AN ACTUATOR AND AN END EFFECTOR

(71) Applicant: TITAN MEDICAL INC., Toronto (CA)

(72) Inventors: Tim Haughton, Newton, MA (US); Rene Robert, East Greenwich, RI (US)

(73) Assignee: Titan Medical Inc. (CA)

( * ) Notice: Subject to any disclaimer, the term of this patent is extended or adjusted under 35 U.S.C. 154(b) by 97 days.

(21) Appl. No.: 15/593,000

(22) Filed: May 11, 2017

(65) Prior Publication Data

US 2018/0325579 A1 Nov. 15, 2018

(51) Int. Cl.
*A61B 18/00* (2006.01)
*A61B 18/14* (2006.01)
(Continued)

(52) U.S. Cl.
CPC .......... *A61B 18/1445* (2013.01); *A61B 34/30* (2016.02); *A61B 90/06* (2016.02);
(Continued)

(58) Field of Classification Search
CPC . A61B 17/28; A61B 17/29; A61B 2017/2901; A61B 2017/2902; A61B 18/1442; A61B 18/1445; A61B 34/30; A61B 90/06; A61B 2090/064; A61B 2018/00178; A61B 2018/00172;
(Continued)

(56) References Cited

U.S. PATENT DOCUMENTS 5,458,598 A * 10/1995 Feinberg ............ A61B 18/1445
606/205
5,571,100 A * 11/1996 Goble ................ A61B 18/1445
606/41

(Continued)

FOREIGN PATENT DOCUMENTS

JP 2008-220971 9/2008

OTHER PUBLICATIONS

U.S. Appl. No. 15/294,477, filed Oct. 14, 2016, U.S. Pat. No. 9,629,688.

(Continued)

*Primary Examiner* — Gary F Paumen
(74) *Attorney, Agent, or Firm* — Knobbe Martens Olson & Bear, LLP

(57) ABSTRACT

A coupler apparatus for coupling electrical signals between an actuator and an end effector is disclosed. The end effector is disposed at a distal end of an elongate articulated positioner and used to position the end effector for performing surgical operations. The articulated positioner has a central lumen and the apparatus includes an elongate body sized to be slidingly received within the central lumen of the articulated positioner, at least a portion of the body being operable to flex during movement of the articulated positioner. The apparatus also includes a plurality of electrical conductors extending through the body, and a plurality of proximal electrical contacts disposed at a proximal end of the body for removably connecting each of the electrical conductors to respective electrical signal lines at the actuator.

13 Claims, 4 Drawing Sheets

(51) Int. Cl.
*A61B 34/30* (2016.01)
*A61B 90/00* (2016.01)
*H01R 24/58* (2011.01)
*H01R 35/04* (2006.01)

(52) U.S. Cl.
CPC ............... *A61B 2018/00172* (2013.01); *A61B 2018/00178* (2013.01); *A61B 2090/064* (2016.02); *H01R 24/58* (2013.01); *H01R 35/04* (2013.01); *H01R 2201/12* (2013.01)

(58) Field of Classification Search
CPC .... H01R 24/58; H01R 2103/00; H01R 35/04; H01R 2201/12
USPC ............. 606/51, 52, 205; 439/668, 669, 909
See application file for complete search history.

(56) References Cited

U.S. PATENT DOCUMENTS

| | | | | |
|---|---|---|---|---|
| 5,716,354 A | * | 2/1998 | Hluchy | A61B 18/1442 606/46 |
| 5,961,514 A | * | 10/1999 | Long | A61B 17/34 606/41 |
| 6,106,519 A | * | 8/2000 | Long | A61B 18/1487 606/32 |
| 6,773,435 B2 | * | 8/2004 | Schulze | A61B 18/1445 606/51 |
| 7,367,973 B2 | * | 5/2008 | Manzo | A61B 18/14 604/22 |
| 9,028,495 B2 | * | 5/2015 | Mueller | A61B 18/1445 606/52 |
| 9,629,688 B2 | * | 4/2017 | Robert | A61B 17/00234 |
| 9,925,014 B2 | * | 3/2018 | Robert | A61B 17/00234 |
| 2009/0005638 A1 | * | 1/2009 | Zwolinski | A61B 1/00087 600/106 |
| 2010/0076433 A1 | * | 3/2010 | Taylor | A61B 18/1445 606/52 |
| 2011/0213360 A1 | * | 9/2011 | Cunningham | A61B 17/29 606/41 |
| 2011/0213361 A1 | * | 9/2011 | Cunningham | A61B 17/29 606/41 |
| 2013/0023923 A1 | * | 1/2013 | Mueller | A61B 17/29 606/205 |
| 2013/0150846 A1 | | 6/2013 | Aue et al. | |
| 2014/0088637 A1 | * | 3/2014 | Parihar | A61B 17/29 606/205 |
| 2015/0157348 A1 | * | 6/2015 | Mueller | A61B 17/29 606/52 |
| 2015/0257820 A1 | * | 9/2015 | Dycus | A61B 18/00 606/51 |
| 2015/0359588 A1 | * | 12/2015 | Allen, IV | A61B 17/285 606/52 |
| 2016/0067001 A1 | * | 3/2016 | Parihar | A61B 18/12 606/52 |
| 2016/0074653 A1 | * | 3/2016 | Anglese | A61B 18/1445 606/51 |
| 2016/0143633 A1 | | 5/2016 | Robert et al. | |
| 2016/0183960 A1 | * | 6/2016 | Stroup | A61B 17/29 606/205 |

OTHER PUBLICATIONS

U.S. Appl. No. 14/899,768, filed Dec. 18, 2015, 2016/0143633 A1.
U.S. Appl. No. 15/442,070, filed Feb. 24, 2017, N/A.
U.S. Appl. No. 15/442,070, filed Feb. 24, 2017, Robert et al.

* cited by examiner

COUPLER APPARATUS FOR COUPLING ELECTRICAL SIGNALS BETWEEN AN ACTUATOR AND AN END EFFECTOR

BACKGROUND

1. Field

This disclosure relates generally to surgical instruments for laparoscopic or robotic surgery and more particularly to a coupler apparatus for coupling electrical signals between an actuator and an end effector.

2. Description of Related Art

Robotic surgical systems commonly employ one or more instruments that are manipulated by a robotic system to perform surgical tasks. Each instrument is generally equipped with an end effector, such as a surgical scissor, grasper, forceps, dissector, or other end effector for performing specific operations. An actuator generally provides for both mechanical and electrical actuation of the end effector. Commonly, the instrument is configured with a specific end effector and changing the end effector may not be possible or may require some disassembly of the instrument.

There remains a need for methods and apparatus for coupling electrically and mechanically between actuators and end effectors.

SUMMARY

In accordance with some embodiments, there is provided a coupler apparatus for coupling electrical signals between an actuator and an end effector. The end effector is disposed at a distal end of an elongate articulated positioner and used to position the end effector for performing surgical operations. The articulated positioner has a central lumen and the apparatus includes an elongate body sized to be slidingly received within the central lumen of the articulated positioner, at least a portion of the body being operable to flex during movement of the articulated positioner. The apparatus also includes a plurality of electrical conductors extending through the body, and a plurality of proximal electrical contacts disposed at a proximal end of the body for removably connecting each of the electrical conductors to respective electrical signal lines at the actuator.

The body may include a plurality of channels extending through the body, each electrical conductor being received in one of the plurality of channels.

The plurality of proximal electrical contacts may be peripherally disposed about an outside surface of the proximal end of the body, each electrical contact being electrically connected to one of the electrical conductors and being operable to make contact with corresponding electrical contacts of the actuator.

The plurality of proximal electrical contacts may include a plurality of annular rings spaced apart on an outside surface of the proximal end of the body, each annular ring being electrically connected to one of the electrical conductors and being operable to make contact with corresponding electrical contacts of the actuator while facilitating rotation of the body with respect to the electrical contacts of the actuator.

The end effector may be irremovably attached to a distal end of the body and the electrical conductors may terminate in electrical contact with portions of the end effector.

The end effector may be removably attached to a distal end of the body and the electrical conductors may each terminate in a distal electrical contact at a distal end of the body, each distal electrical contact being operable to make contact with a corresponding contact of the end effector when connected to the distal end of the body.

The body may be operably configured to provide a degree of torsional rigidity and the actuator may include a mechanical interface for receiving and retaining the body, the mechanical interface being further operable to deliver a rotational torque to the body for causing rotation of the end effector.

The body may include a central conduit for slidably receiving a control link, the control link extending between the actuator and the end effector for causing mechanical actuation of the end effector.

The body may have a generally cylindrical shape.

The plurality of channels may be arranged spaced apart about a longitudinal axis of the body.

The body may include a plurality of coaxial insulating sheaths defining a plurality of annular cylindrical channels each having an electrical conductor received therein.

The plurality of coaxial insulating sheaths may include a centrally disposed insulating sheath having a central conduit for slidably receiving a control link, the control link extending between the actuator and the end effector for causing mechanical actuation of the end effector.

The control link may include a conductive material and acts as one of the electrical conductors.

In accordance with some embodiments, there is provided an actuator apparatus operable to receive the coupling apparatus above, the actuator apparatus including a mechanical interface for receiving and retaining the body, and a plurality of actuator electrical contacts for making electrical contact with respective proximal electrical contacts on the body.

The mechanical interface may be operable to transmit a rotational torque for rotating the body, and the plurality of actuator electrical contacts may be operably configured to maintain electrical connection with the respective proximal electrical contacts during rotation of the body.

The mechanical interface may include an opening for receiving and retaining the proximal end of the body, and a rotatable spool, the plurality of actuator electrical contacts being disposed within the opening of the mechanical interface and connected to a length of electrical conductor wound around the spool, the spool being operable to permit rotation of the mechanical interface while playing out or taking up the electrical conductor lengths.

Other embodiments and features will become apparent to those ordinarily skilled in the art upon review of the following description of specific disclosed embodiments in conjunction with the accompanying figures.

BRIEF DESCRIPTION OF THE DRAWINGS

In drawings which illustrate disclosed embodiments.

DETAILED DESCRIPTION

Figure 1:
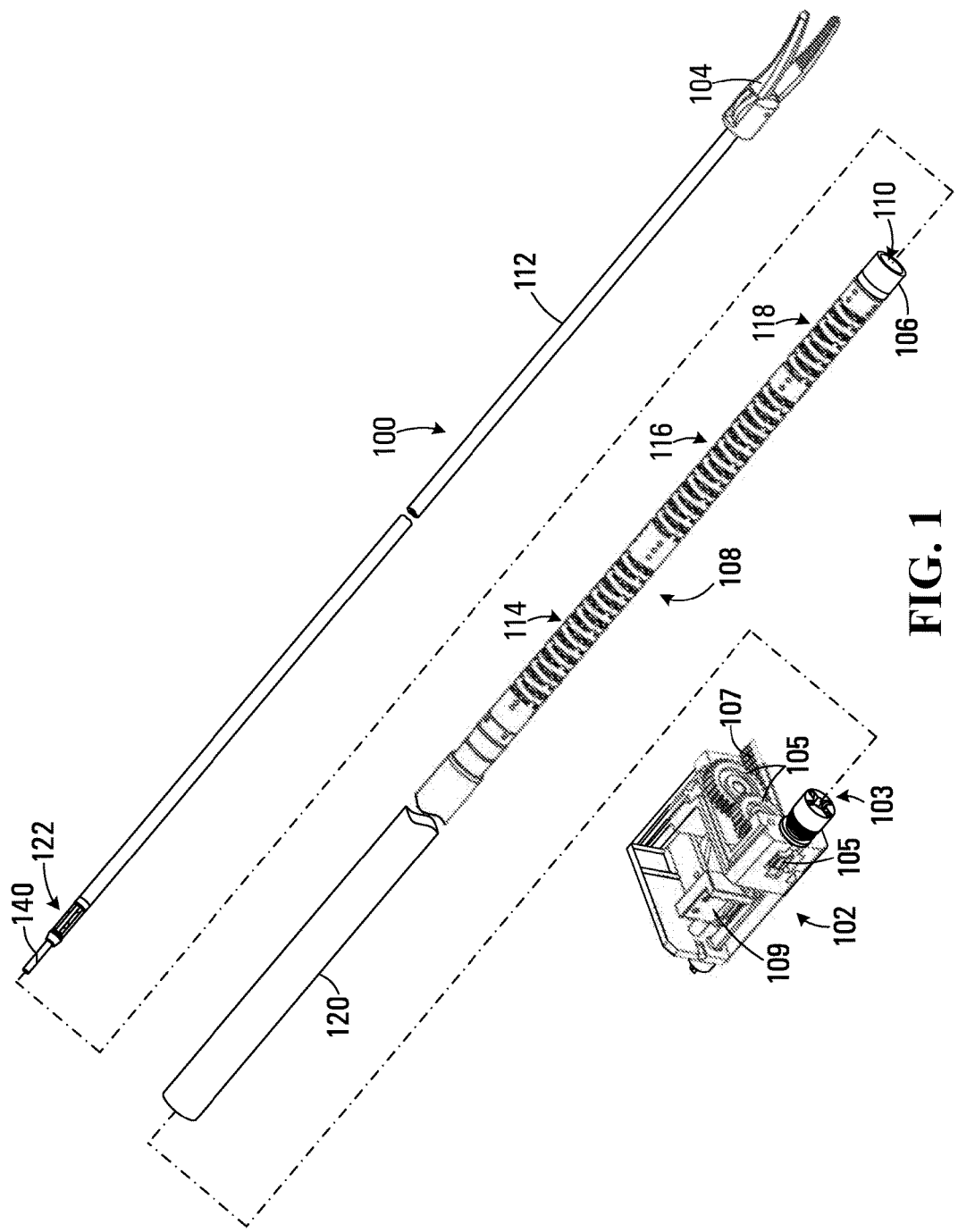
FIG. 1 is a perspective exploded view of a couple apparatus, end effector, tool positioner, and actuator in accordance with one embodiment.

Referring to FIG. 1, a coupler apparatus according to an embodiment is shown generally at 100. The coupler apparatus 100 is operable to route electrical signals between an actuator 102 and an end effector 104 disposed at a distal end 106 of an elongate articulated positioner 108. The actuator 102 may be part of a robotic surgical system (not shown) for performing surgical operations on a living human or other animal by manipulating the end effector 104. The actuator includes a mechanical interface 103 for receiving the coupler apparatus 100 and may be operable to provide mechanical actuation of the positioner 108, coupler apparatus 100, and the end effector 104 such as described in commonly owned PCT patent application PCT/CA2015/000098 entitled "ACTUATOR AND DRIVE FOR MANIPULATING A TOOL" filed on Feb. 18, 2015 and incorporated herein by reference in its entirety. The positioner 108 has a central lumen 110 and is used to position the end effector 104 for performing surgical operations. The positioner 108 may be a tool positioner such as the tool positioner described commonly owned patent application PCT/CA2013/001076 entitled "ARTICULATED TOOL POSITIONER AND SYSTEM EMPLOYING SAME" filed on Dec. 20, 2013 and incorporated herein by reference in its entirety. The coupler apparatus 100 includes an elongate body 112 sized to be slidingly received within the central lumen 110 of the articulated positioner 108. In the embodiment shown the body 112 has a generally cylindrical shape.

In the embodiment shown the positioner 108 includes three articulated sections 114, 116, and 118, which are manipulated by control links (not shown) to bend transversely causing the distal end 106 of the positioner to move to a desired location and orientation in three-dimensional space. The positioner 108 also includes a rigid unarticulated section 120. The body 112 of the coupler apparatus 100 has at least a portion that is operable to flex during movement of the articulated positioner. In one embodiment the entire body 112 may be fabricated from a flexible material. In other embodiments only a portion that is required to flex within the articulated sections 114, 116, and 118 of the positioner 108 may be flexible while the remaining body portion is rigid or substantially rigid.

Figure 2:
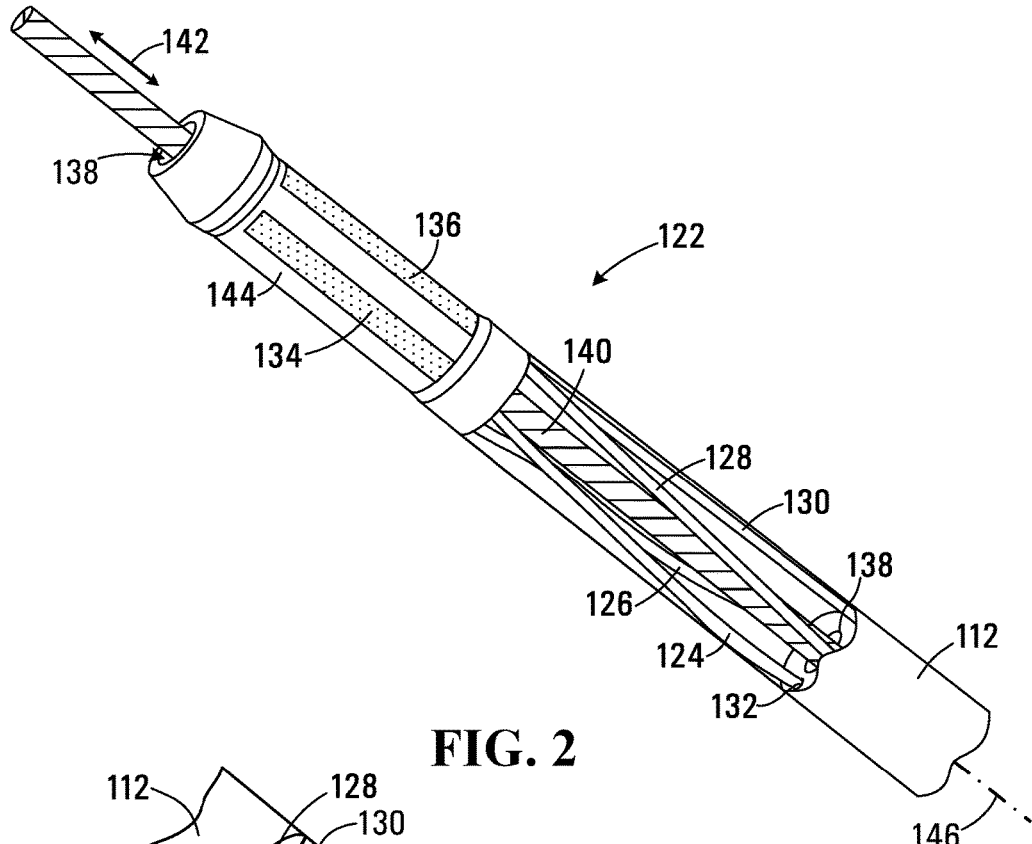
FIG. 2 is a perspective view of a proximal end of the coupler apparatus shown in FIG. 1.

The coupler apparatus 100 has a proximal end 122 that is sized to be received in the central lumen 110 of the positioner 108. The proximal end 122 of the coupler apparatus 100 is shown in enlarged detail with a portion of the body 112 cut away in FIG. 2. Referring to FIG. 2, the body 112 of the coupler apparatus 100 has a plurality of electrical conductors 124, 126, 128, and 130 extending through the body. In this embodiment, the body 112 has a plurality of channels for receiving each respective electrical conductor 124-130 (for example, the conductor 124 is shown received within a channel 132 in FIG. 2). The plurality of channels are arranged spaced apart about a longitudinal axis 146 of the body 112.

The proximal end 122 of the coupler apparatus 100 also includes a plurality of proximal electrical contacts disposed at the proximal end 122 for removably connecting each of the electrical conductors 124-130 to respective electrical signal lines at the actuator 102. In FIG. 2, an electrical contact 134 is associated with the electrical conductor 124 and an electrical contact 136 is associated with the electrical conductor 128. Further contacts (not visible in FIG. 2) are provided on an underside of the proximal end 122 of the coupler apparatus 100. The electrical contacts 134 and 136 are peripherally disposed about an outside surface 144 of the proximal end 122 and each electrical contact is electrically connected to a respective one of the electrical conductors 124 and 128. Similarly, electrical contacts on the underside of the outside surface 144 of the proximal end 122 are connected to the respective electrical conductors 126 and 130. In the embodiment shown the electrical contacts 134 and 136 comprise conductive strips disposed on an insulating outside surface 144 of the proximal end 122 of the body 112.

In this embodiment the body 112 includes a central conduit 138 for slidably receiving a control link 140. The control link 140 extends through the central conduit 138 and couples to the actuator 102 for causing mechanical actuation of the end effector 104 through longitudinal movements of the control link in the direction indicated by the arrow 142. The coupler apparatus 100 shown in FIG. 1 and FIG. 2 includes four electrical conductors 124-130 that terminate in electrical contact with portions of the end effector 104 and may be used to deliver an electrocauterization current to tissue grasped or in contact with the end effector 104. Some of the electrical conductors 124-130 may also be able be used to deliver other electrical signals to or from the end effector 104 including signals received from sensors coupled to the end effector for detecting forces, temperatures, or other information. In other embodiments the coupler apparatus 100 may include a fewer number of conductors for driving a bipolar or monopolar end effector. Alternatively, more than four conductors may be provided for end effectors that require additional signals for operation.

Figure 3:
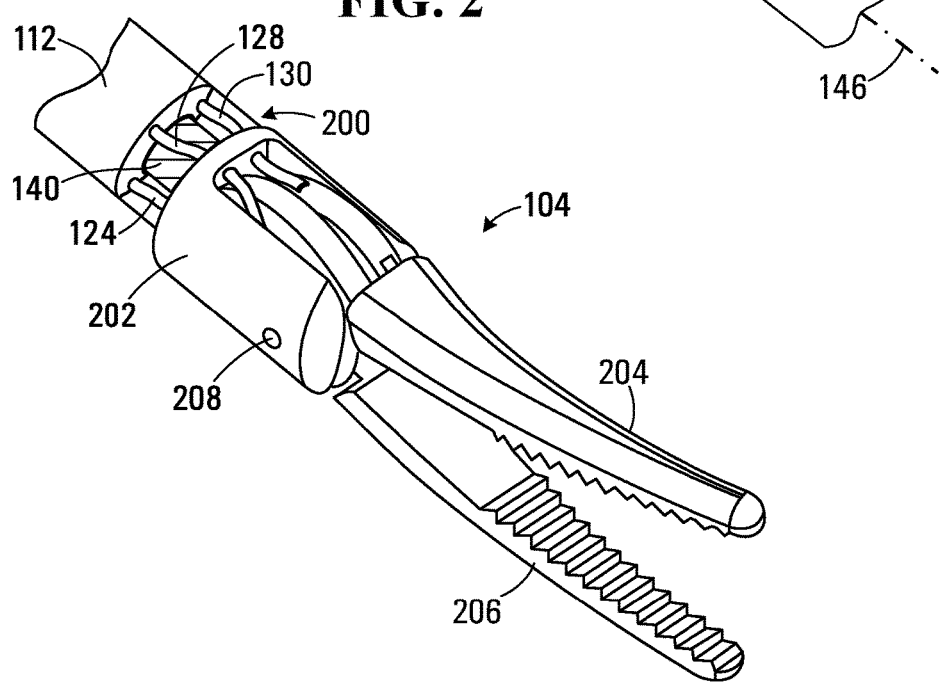
FIG. 3 is a perspective view of the end effector shown in FIG. 1.

Referring to FIG. 3, the end effector 104 is shown in enlarged detail connected to a distal end 200 of the body 112 of the coupler apparatus 100. In this embodiment the end effector 104 is irremovably attached to the distal end 200 of the coupler apparatus body 112 and the coupler apparatus 100 and end effector 104 may be packaged as a sterile unit for limited-use and subsequent disposal. A portion of the coupler apparatus 100 is shown cut way in FIG. 3 to show the electrical conductors 124, 128, and 130 (the electrical conductor 126 is below the control link 140 and not visible in FIG. 3). The end effector 104 includes a hub 202 and a pair of opposing electrically conductive jaws 204 and 206 mounted on a pivot 208 extending through the hub. The control link 140 is coupled to the jaws 204 and 206 via a yoke mechanism (not shown) within the hub 202 that causes the jaws to open or close to grasp or otherwise contact tissue.

The electrical conductor 130 extends through the hub 202 and connects to the jaw 204 while the electrical conductor 124 similarly connects to the jaw 206 for supplying an electrocauterization current to tissue grasped between the jaws 204 and 206. In this embodiment the hub 202 and yoke and jaws 204 and 206 may be fabricated from a metal material, with the jaws being insulated so as to permit individual connection of electrocauterization current to the jaws. Additional conductors 126 and 128 may be used for a two-wire supply to a heating element within the jaw, for example or to carry other electrical signals to the end effector 104.

Referring back to FIG. 1, in the embodiment shown the actuator 102 includes a gear train 105 driven by a linear rack gear 107 for causing rotation of the mechanical interface to transmit a rotational torque to the body 112 for causing a respective rotation of the end effector 104.

Figure 4:
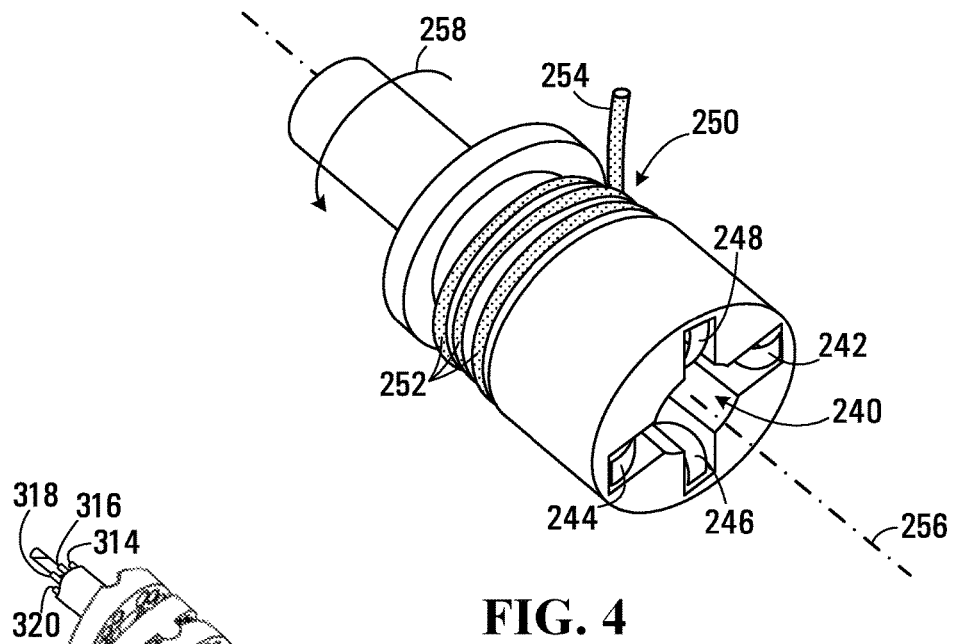
FIG. 4 is a perspective view of a mechanical interface of the actuator shown in FIG. 1.

The mechanical interface 103 of the actuator 102 is shown in enlarged detail in FIG. 4. Referring to FIG. 4, the mechanical interface 103 includes a central opening 240 sized to receive and retain the proximal end 122 of the body 112 of the coupler apparatus 100. The body 112 is configured to provide a degree of torsional rigidity for causing rotation of the end effector 104 in response to a rotational torque imparted by the mechanical interface 103. The actuator 102 also includes actuator electrical contacts 242, 244, 246, and 248 accommodated in respective channels in the actuator. The electrical contacts 242, 244, 246, and 248 correspond to the electrical contacts on the proximal end 122 of the coupler apparatus 100 (i.e. contacts 134 and 136 shown in FIG. 2 correspond to contacts 244 and 246 on the actuator).

The actuator 102 further includes a rotatable spool 250 for receiving a length of electrical conductor 254 wound around the spool and connecting to the electrical contacts 242, 244, 246, and 248. The electrical conductor 254 is routed back to a signal source of the tool interface (not shown). In this embodiment the electrical conductor 254 is a four core flexible cable, but in other embodiments separate electrical conductors may be received on the spool 250. In other embodiments, the rotatable spool 250 may be driven by other means to impart a roll motion on the rotatable spool. For example, a geared drive mechanism may be in direct contact with a geared interface on a surface of the rotatable spool, with a signal being delivered through at least a portion of the geared drive mechanism and a corresponding portion of the geared interface that are respectively made of conductive materials for providing electrical connection.

When the actuator 102 causes the rotatable spool 250 to rotate about its longitudinal axis 256 in a direction indicated by arrow 258, the windings 252 on the spool 250 play out allowing at least one rotation of the actuator 102. Similarly when rotated opposite to the direction indicated by arrow 258, the spool 250 takes up further windings of the electrical conductor 254 allowing rotation of the mechanical interface 103. The spool 250 will generally be configured to take up a sufficient number of windings 252 to permit rotation of the mechanical interface 103 for actuating rotation of the body 112 and the end effector 104 through an angle (in one embodiment through an angle of about ±315°), Referring back to FIG. 2, when the proximal end 122 of the coupler apparatus 100 is inserted into the central opening 240, the electrical contacts 134 and 136 and contacts on the underside of the outside surface 144 of the coupler apparatus 100 make sliding electrical contact with the corresponding electrical conductors 242-246 in the mechanical interface 103 and thus with corresponding conductors in the electrical conductor 254. The electrical contacts 242, 244, 246, and 248 are operably configured to maintain electrical connection with the respective proximal electrical contacts on the proximal end 122 of the body 112 during rotation of the mechanical interface 103 and the body.

Figure 8:
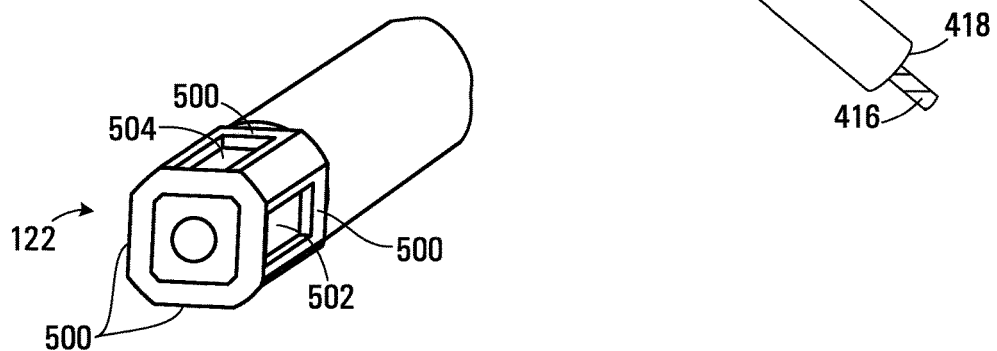
FIG. 8 is a perspective view of another embodiment for the proximal end of the coupler apparatus shown in FIG. 1 and FIG. 2.

Referring to FIG. 8, in other embodiments, the proximal end 122 of the coupler apparatus 100 may have a non-circular shape providing one or more locking or keyed surfaces 500 that have corresponding surface features within the central opening 240 of the mechanical interface 103 for preventing rotation of the proximal end of the body of the coupler apparatus. The locking or keyed surfaces 500 assist in establishing electrical contact between contacts (contacts 502 and 504 are visible in FIG. 8) and the contacts 242, 244, 246, and 248 of the actuator 102. The locking or keyed surfaces 500 prevent rotational slippage between the coupler apparatus 100 and the actuator 102 that may occur during rotational movement of the actuator.

In other embodiments, the electrical contacts 134, 136 may extend outwardly from the surface 144 of the coupler apparatus and engage with the electrical contacts 242, 244, 246, and 248 to provide the necessary transmission of rotational forces between the actuator 102 and the proximal end 122 of the coupler apparatus 100.

Referring back to FIG. 1, in operation the coupler apparatus 100 and end effector 104, if supplied as a sterile unit, may be unpacked and inserted through the distal end 106 of the positioner 108 and through the central lumen 110. The proximal end 122 of the coupler apparatus is then received in the central opening 240 of the mechanical interface 103 making electrical contact between the tool interface and the coupler apparatus 100. The control link 140 passes through the actuator 102 and may be coupled to a control link actuator 109 (shown in FIG. 1) for actuating longitudinal movements of the control link. On completion of the surgery, the coupler apparatus 100 and end effector 104 may be removed from the positioner 108 and discarded. The positioner 108 may then be sterilized for subsequent use. The disposable configuration of the coupler apparatus 100 avoids the need to sterilize the central conduit 138 coupler apparatus 100, which may be difficult to flush due to its relatively narrow diameter.

Figure 5:
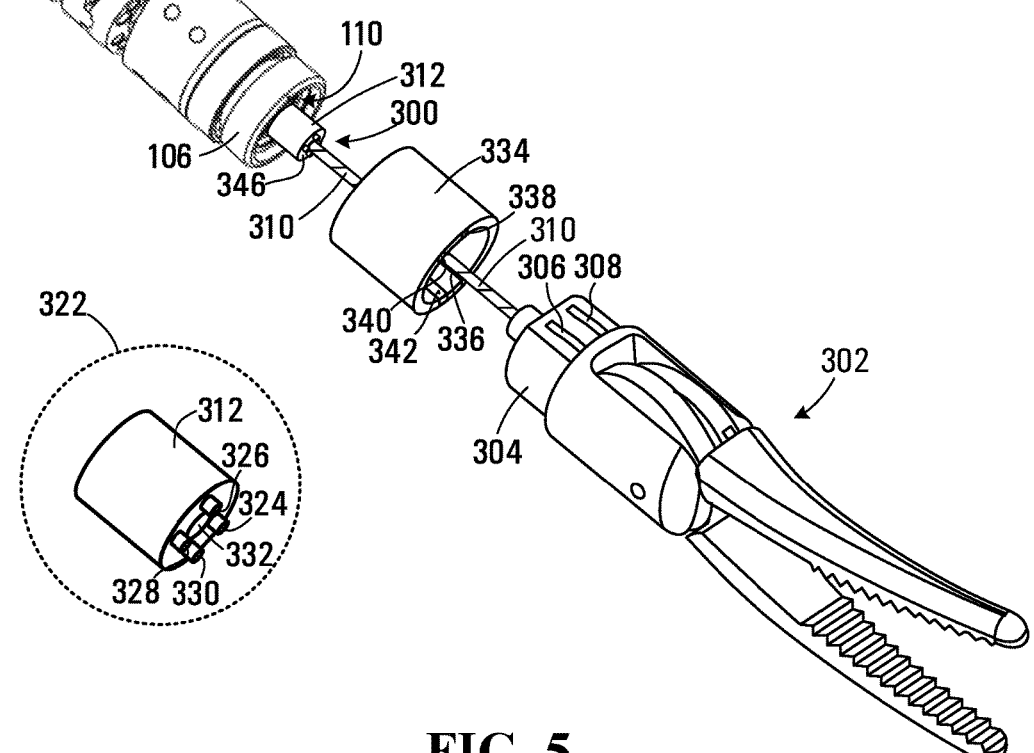
FIG. 5 is a perspective exploded view of an another embodiment of a coupler apparatus.

Referring to FIG. 5, an embodiment of a coupler apparatus is shown in exploded view generally at 300. In this coupler embodiment an end effector 302 includes a connector portion 304 having a plurality of electrical contacts. In FIG. 5 two electrical contacts 306 and 308 are shown configured as conductive strips disposed on the connector portion 304, which is non-conductive. A further pair of electrical contacts may be disposed on the underside of the connector portion 304. The end effector 302 includes a control link 310 connected to the end effector and may be supplied as a sterile unit. A portion of the positioner 108 is also shown in FIG. 5 with the coupler apparatus 300 already inserted into the central lumen 110. The coupler apparatus 300 includes a body 312 having channels for receiving electrical conductors 314, 316, 318, and 320. The electrical conductors 314-320 each have a conductive portion that protrudes from a distal end 346 of the body 312, providing distal electrical contacts 324, 326, 328 and 330 (shown in the insert 322) at the distal end. The body 312 also has a central conduit 332 running through the body for receiving the control link 310.

The end effector 302 may be connected to the positioner 108 via a distal coupler 334 that includes electrical contacts 336, 338, 340, and 342, which make sliding electrical contact with the contacts 304, 306, and the contacts disposed on the underside of the connector portion 304 of the end effector. The distal coupler 334 is shaped to receive the connector portion 304, and the distal coupler 334 and connector portion 304 of the end effector 302 may snap or clip together to retain the end effector on in the coupler and the distal coupler 334 may be attached to the distal end 106 of the positioner 108.

Figure 6:
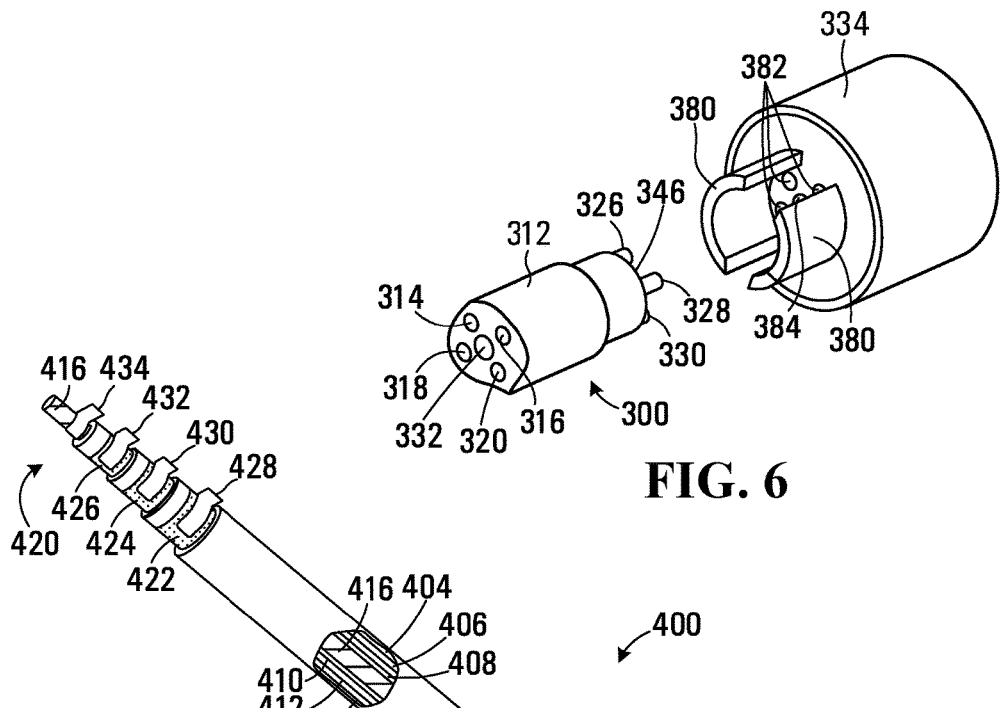
FIG. 6 is a rear perspective view of a distal coupler and a distal end of the coupler apparatus shown in FIG. 5.

The distal end 346 of the coupler apparatus 300 and distal coupler 334 are shown from a rear perspective in FIG. 6. The distal coupler 334 includes a cylindrical guide portion 380 for receiving the distal end 346 of the coupler apparatus 300. The distal coupler 334 also includes a plurality of contacts 382 (one of which is fully visible, two partially obscured, and one completely obscured in FIG. 6). The plurality of contacts 382 make electrical contact with the respective contacts 326-330 on the coupler apparatus 300 when the distal end 346 of the body 312 is received in the cylindrical guide portion 380 of the distal coupler 334. The distal coupler 334 also includes a central opening 384 for receiving the control link 310. The distal coupler 334 thus acts as a mechanical and electrical interface between the end effector 302 and the positioner 108. In FIG. 6, portions of the electrical conductors 314-320 are visible from the rear, each being received in a respective channel in the body 312. The central conduit 332 also extends through the body for receiving the control link 310.

In operation, the end effector 302 may be packed as a sterile unit including the control link 310. The positioner 108 is prepared with the coupler apparatus 300 inserted through its central lumen 110 as shown in FIG. 5 such that the distal end 346 protrudes slightly from the central lumen. The distal coupler 334 is then attached to the distal cylindrical portion 344 of the positioner 108 making electrical contact between the contacts 326-330 on the distal end 346 of the coupler apparatus 300 and the corresponding contacts 382 on the distal coupler 334. Finally the control link 310 is threaded through the central opening 384 of the distal coupler 334 and through the central conduit 332 in the coupler apparatus 300. The contacts 306 and 308 on the connector portion 304 of the end effector 302 are then pressed into engagement with the contacts 336-340 on the distal coupler 334 making electrical connection to the end effector 302 through the coupler apparatus 300. The embodiment shown provides for visible electrical connection between the end effector 302 and the distal coupler 334.

In one embodiment, a proximal end of the coupler apparatus 300 may be configured with electrical contacts, such as shown at 334 and 336 in FIG. 2 for use with a mechanical interface such as shown at 103 in FIG. 4.

Figure 7:
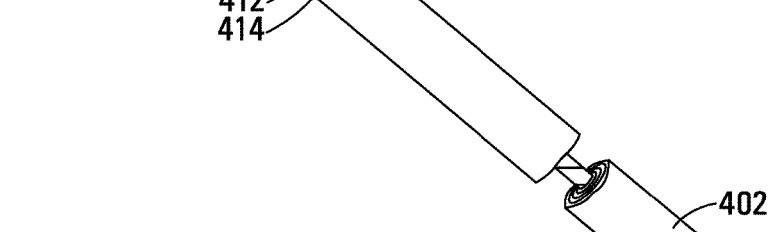
FIG. 7 is a perspective view of another embodiment of a coupler apparatus.

Referring to FIG. 7, an embodiment of coupler apparatus is shown generally at 400. The coupler apparatus 400 includes a body 402 having a plurality of coaxial insulating sheaths 404, 406, and 408 defining a plurality of annular cylindrical channels having respective electrical conductors 410, 412, and 414 received therein. The coupler apparatus 400 also includes a control link 416, which may be electrically conductive thus providing a fourth electrical conductor. A distal end 418 connects to an end effector (not shown) using a configuration generally as shown in either FIG. 3 or FIG. 5 or other connection configuration. A proximal end 420 of the coupler apparatus 400 includes a plurality of electrically conductive annular rings 422, 424, and 426, which are in electrical contact with the respective electrical conductors 410, 412, and 414. The proximal end 420 of the coupler apparatus 400 is sized to be received within a mechanical interface of an actuator, generally as shown at 102 and 103 in FIG. 1. In this embodiment the mechanical interface includes a plurality of leaf springs that act as electrical connectors 428, 430, 432, and 434 that make sliding electrical contact with the electrical conductors 410-414 and an outer conductive surface of the control link 416. The electrical connectors 428, 430, 432, and 434 are disposed within a mechanical interface and permit rotation of the coupler apparatus 400 and also permit longitudinal movement of the control link 416 for actuating an end effector.

In one embodiment the body 402 of the coupler apparatus 400 may be made from materials that withstand temperatures during sterilization by autoclaving. The coupler apparatus 400 and an attached end effector may thus be reprocessed and reused for a set number of uses, thus reducing operating cost. In one embodiment the coupler apparatus 400 may be provided with an electronic use counter or identifier that can be tracked to record the number of uses. After a pre-determined number of uses the coupler apparatus may be discarded.

Various disclosed features of above embodiments may be used in combinations other than disclosed above. For example, the various disclosed distal connections may be combined with other proximal connections than shown in the above figures.

Methods of using the disclosed system is included; a method of use can include using or assembling any one or more of the foregoing features to achieve functions and/or features of the disclosed systems. A method of manufacturing the foregoing system is included; the method of manufacture can include providing, making, connecting, assembling, and/or installing any one or more of the foregoing features of the system to achieve functions and/or features of the system as discussed in this disclosure.

Features, materials, characteristics, or groups described in conjunction with a particular aspect, embodiment, or example are to be understood to be applicable to any other aspect, embodiment or example described herein unless incompatible therewith. All of the features disclosed in this specification (including any accompanying claims, abstract and drawings), or all of the steps of any method or process so disclosed, may be combined in any combination, except combinations where at least some of such features or steps are mutually exclusive. The protection is not restricted to the details of any foregoing embodiments. The protection extends to any novel one, or any novel combination, of the disclosed features (including any accompanying claims, abstract and drawings), or to any novel one, or any novel combination, of the steps of any method or process so disclosed.

Conditional language, such as "can," "could," "might," or "may," unless specifically stated otherwise, or otherwise understood within the context as used, is generally intended to convey that certain embodiments include, while other embodiments do not include, certain features, elements, or steps. Thus, such conditional language is not generally intended to imply that features, elements, or steps are in any way required for one or more embodiments or that one or more embodiments necessarily include logic for deciding, with or without user input or prompting, whether these features, elements, or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount.

The scope of the present disclosure is not intended to be limited by the specific embodiments described, and may be defined by claims as presented now or in the future. The language of the claims is to be interpreted broadly based on the language employed in the claims and not limited to the examples described in the present specification or during the prosecution of the application, which examples are to be construed as non-exclusive.

What is claimed is:

1. A coupler apparatus for coupling electrical signals between an actuator and an end effector disposed at a distal end of an elongate articulated positioner and used to position the end effector for performing surgical operations, the articulated positioner having a central lumen, the apparatus comprising:
   an elongate body sized to be slidingly received within the central lumen of the articulated positioner, wherein at least a portion of the body is configured to flex during movement of the articulated positioner;
   a plurality of electrical conductors extending through the body; and
   a plurality of proximal electrical contacts disposed at a proximal end of the body configured to removably connect each of the electrical conductors to respective electrical signal lines at the actuator.

2. The apparatus of claim 1 wherein the body comprises a plurality of channels extending through the body, each electrical conductor being received in one of the plurality of channels.

3. The apparatus of claim 1 wherein the plurality of proximal electrical contacts are peripherally disposed about an outside surface of the proximal end of the body, each electrical contact being electrically connected to one of the electrical conductors and configured to make contact with corresponding electrical contacts of the actuator.

4. The apparatus of claim 1 wherein the plurality of proximal electrical contacts comprise a plurality of annular rings spaced apart on an outside surface of the proximal end of the body, each annular ring being electrically connected to one of the electrical conductors and configured to make contact with corresponding electrical contacts of the actuator while facilitating rotation of the body with respect to the electrical contacts of the actuator.

5. The apparatus of claim 1 wherein the end effector is irremovably attached to a distal end of the body and wherein the electrical conductors terminate in electrical contact with portions of the end effector.

6. The apparatus of claim 1 wherein the end effector is removably attached to a distal end of the body and wherein the electrical conductors each terminate in a distal electrical contact at a distal end of the body, each distal electrical contact configured to make contact with a corresponding contact of the end effector when connected to the distal end of the body.

7. The apparatus of claim 1 wherein the body is configured to provide a degree of torsional rigidity and wherein the actuator comprises a mechanical interface configured to receive and retain the body, the mechanical interface further configured to deliver a rotational torque to the body to cause rotation of the end effector.

8. The apparatus of claim 1 wherein the body comprises a central conduit configured to slidably receive a control link, the control link extending between the actuator and the end effector and configured to cause mechanical actuation of the end effector.

9. The apparatus of claim 1 wherein the body has a generally cylindrical shape.

10. The apparatus of claim 2 wherein the plurality of channels are arranged spaced apart about a longitudinal axis of the body.

11. The apparatus of claim 9 wherein the body comprises a plurality of coaxial insulating sheaths defining a plurality of annular cylindrical channels each having an electrical conductor received therein.

12. The apparatus of claim 11 wherein the plurality of coaxial insulating sheaths comprise a centrally disposed insulating sheath having a central conduit configured to slidably receive a control link, the control link extending between the actuator and the end effector and configured to cause mechanical actuation of the end effector.

13. The apparatus of claim 12 wherein the control link comprises a conductive material and acts as one of the electrical conductors.

* * * * *